United States Patent [19]

Sinila

[11] Patent Number: 5,538,214
[45] Date of Patent: Jul. 23, 1996

[54] LOCKING ACCESSORY SUPPORT APPARATUS

[76] Inventor: Alexander Sinila, 224 Beverly Rd., Barrington, Ill. 60010

[21] Appl. No.: 281,467

[22] Filed: Jul. 27, 1994

[51] Int. Cl.$^6$ ....................................................... E04G 3/00
[52] U.S. Cl. .................................... 248/278.1; 248/284.1
[58] Field of Search .......................... 248/123.11, 278.1, 248/280.11, 284.1, 292.11; 188/74, 80

[56] References Cited

U.S. PATENT DOCUMENTS

| | | | |
|---|---|---|---|
| 3,820,752 | 6/1974 | Oram | 248/278 |
| 4,160,536 | 7/1979 | Krogsrud. | |
| 4,221,353 | 9/1980 | Kuhn et al.. | |
| 4,266,747 | 5/1981 | Souder, Jr. et al.. | |
| 4,500,251 | 2/1985 | Kiryu et al. | 248/123.1 X |
| 4,545,555 | 10/1985 | Koch | 248/280.1 |
| 4,664,232 | 5/1987 | Takagi et al. | 188/74 |
| 4,828,323 | 5/1989 | Brodersen et al. | 248/284 X |
| 4,969,625 | 11/1990 | Singer et al.. | |
| 4,989,229 | 1/1991 | Negrelli et al.. | |
| 5,029,674 | 7/1991 | Boyes et al. | 188/74 X |

FOREIGN PATENT DOCUMENTS

| | | | |
|---|---|---|---|
| 574412 | 3/1959 | Canada | 248/284 |

*Primary Examiner*—Ramon O. Ramirez
*Assistant Examiner*—Derek J. Berger
*Attorney, Agent, or Firm*—Kajane McManus

[57] ABSTRACT

A device to support an appliance such as a pre-amplifier, in a desired position, free of gravitational drifting. The apparatus does not depend on counter-balancing springs to maintain its position, but becomes a constrained mechanism fixing its position. Having a convenient and quick method for releasing the constraint during re-positioning of the subject appliance.

4 Claims, 5 Drawing Sheets

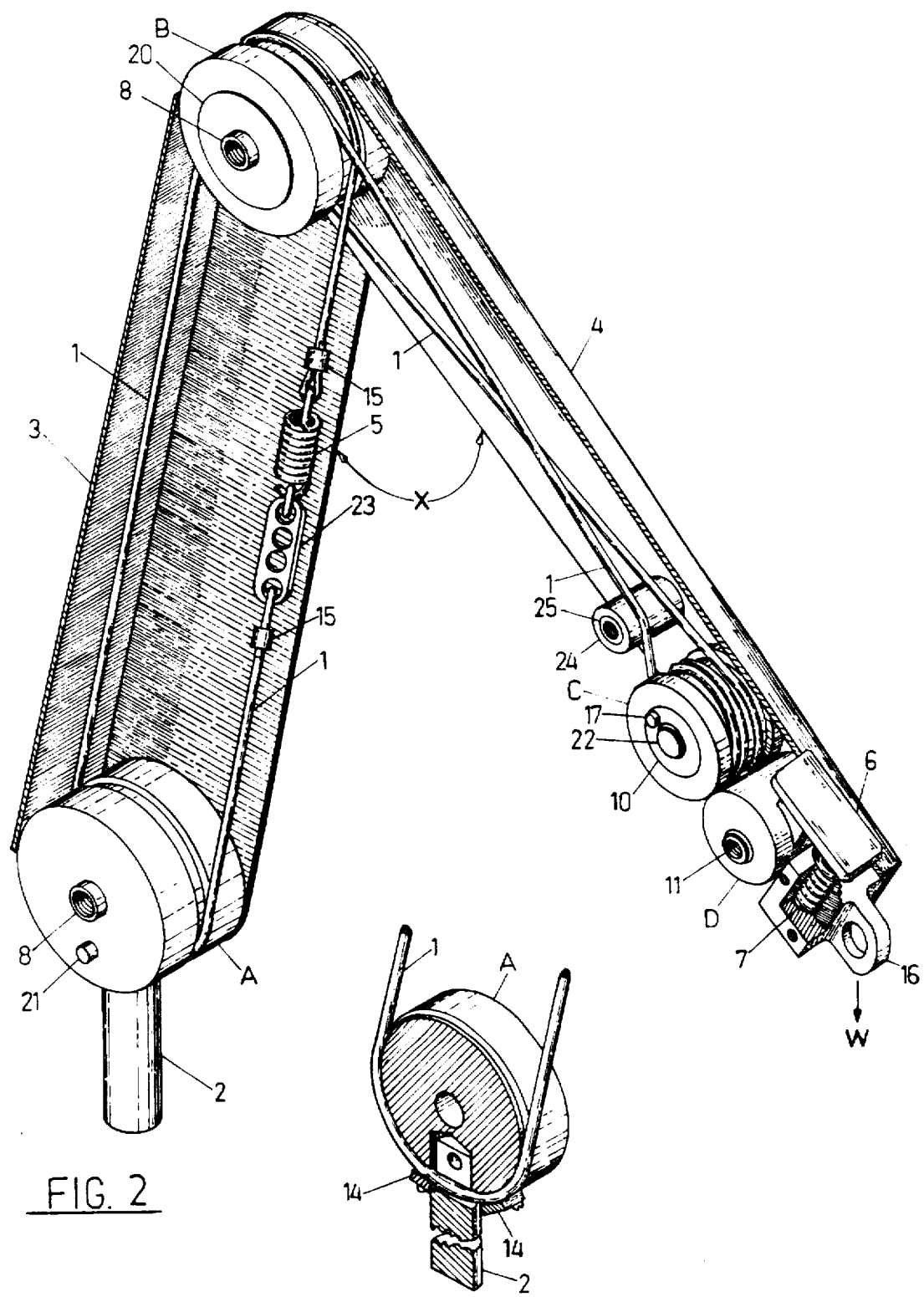

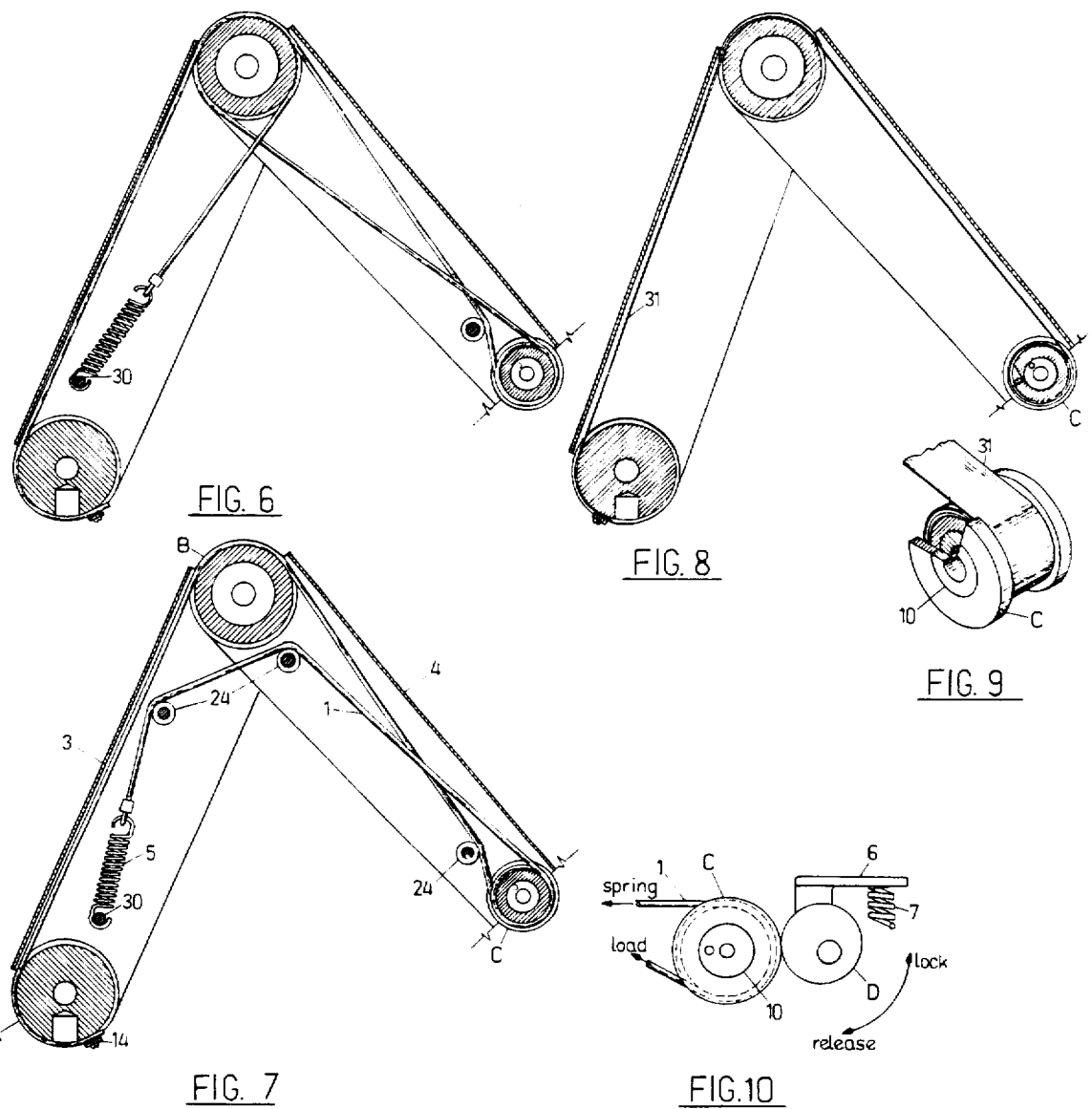

LOCKING ACCESSORY SUPPORT APPARATUS

BACKGROUND

1. Field of the Invention

This invention relates to solving problems encountered in supporting, an instrument or other type of accessory, in various stable positions. It primarily resulted in the specific need of supporting, an instrument pre-amplifier, in close proximity to a patient undergoing a medical examination. A case where the need for the connecting leads between patient and the input to the pre-amplifier be as short as possible.

2. Description of Prior Art

This mechanism is unlike the ubiquitous support devices usually found in such items as desk lamps. The usual mechanisms depend on the approximating counter-balancing force of springs and pivotal friction. Since the stability of position is dependent on these forces, they are only truly balanced for non-variable and mostly static forces. When these ubiquitous support devices are used for applications other than lamp supports, their repeated positioning induces wear on the pivots destroying the integrity of the original friction forces plus any variable loading make these devices not conveniently effective to accomplish their intended purpose.

The mechanism described in this invention overcomes the above deficiencies since it is not dependent on spring forces to balance the forces of gravity. It becomes a constrained, fixed linkage, when subjected to the gravitational load of the supported object or appliance. It is useful as a support over a much wider range of weights than those of dedicated spring counter-balanced devices. Thus there is no gravitational drifting of position to cause annoyance and agrivation to its user.

Unlike the ubiquitous spring balanced parallelogram device described as prior art, this mechanism is a linkage to provide support and variable positioning to a physical item of interest and to maintain its selected position without any drifting from this position due to gravitational forces resulting from the weight of the supported object or mechanism. It is especially useful in applications where repeated specific position changes are required during an on going procedure. An example would be; such as supporting an input device during a physical examination of a prone or supine patient, especially when the input device must be located near various and changing examination sites.

It should be noted that a release lever is located adjacent to the appliance in use, thus facilitating easy access for its operation, a definite advantage, since this is always in the convenient proximity of the operator.

OBJECT AND SUMMARY OF THE INVENTION

The objective of this invention is to provide a mechanism for the stable positioning of an accessory in close proximity to its area of utility.

It includes a mounting spindle that mounts into a bracket usually located on the primary apparatus such as an Electromyograph or Evoked Response console. This spindle is able to rotate in this bracket thus allowing the entire mechanism to rotate in a horizontal plane. To this spindle a lower arm is pivotly attached, also the opposite end of this arm is pivotly attached to second or outer arm. At the opposite end of this outer arm is afixed a mounting for an accessory and a lever for actuating the release of the lock on the mechanism.

To define the invention into a specified configuration a flexible tensile element is employed which locks the desired vertical position of the subject accessory. Releasing the lock, as with slight thumb pressure on the control lever allows easy re-configuration and re-positioning of the subject accessory.

Thus the vertical position locking capability together with the freedom of horizontal rotation results in complete three dimensional positioning in the area of interest.

BRIEF DESCRIPTION OF THE DRAWINGS

FIG. 2. Is an isometric cutaway view of the main items of the invention with part of each arm removed so as to facilitate the explanation of its operation and costruction.

FIG. 3. Cross-section pictorial of Cylinder A, Spindle 2 and Cable clamping details.

FIG. 6. Pictorial of path of flexible element 1 that increases spring tension only with rotation of link 3.

FIG. 7. Pictorial of path of flexible element 1 that increases spring tension with rotation of arm 3 and extension of arm 4.

FIG. 8. Shows use of alternate flexible element that also functions as a retractive spring element.

FIG. 9. Detail showing multiple revolutions of metal tape spring around modified capstan pulley.

FIG. 10. Isolated detail of capstan cylinder C, and locking cylinder D. This is the preferred embodiment of locking Capstan cylinder C but is not limited to this method.

OPERATION

Figure 1:
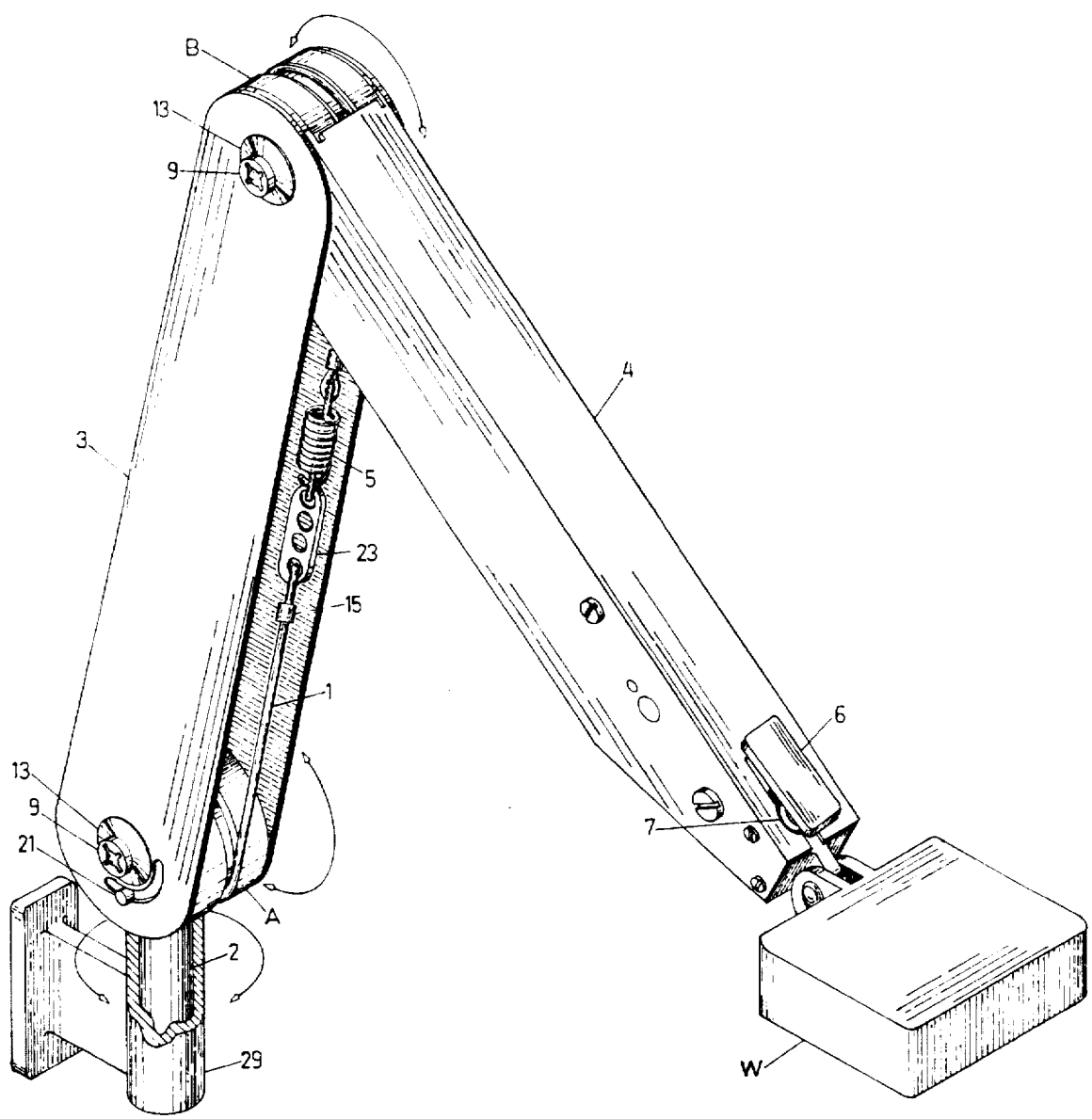
FIG. 1. Is an isometric view of the invention mounted in an appropriate bracket with a symbolic load (W) attached.
Figure 4:
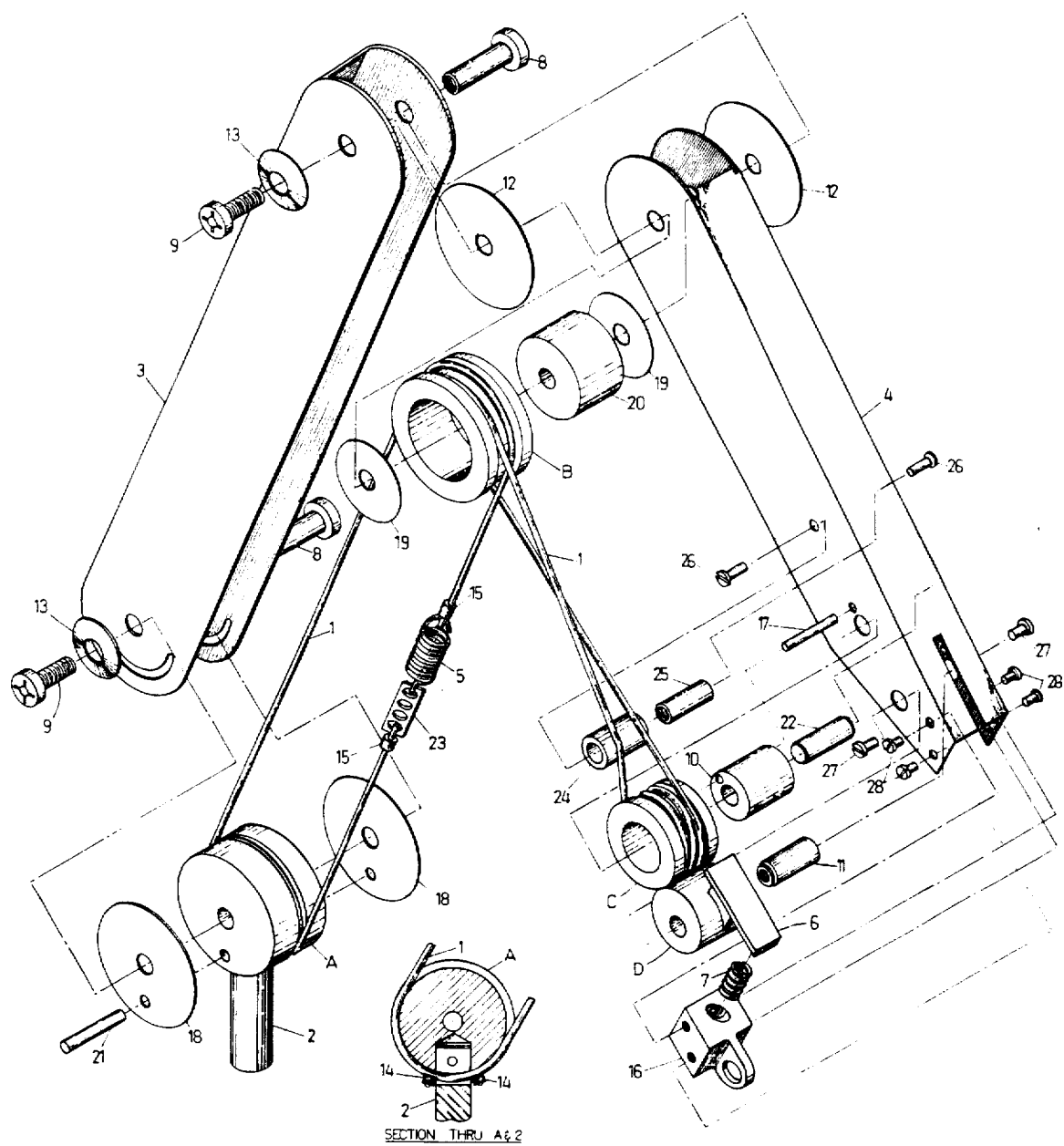
FIG. 4. Shows an exploded view of the prototype to aid in clarifying any ambiguities that may exist in other figures.

To explain the operation of this device FIGS. 1,2,3 and 4 are appropriate and are denoted by a common nomenclature. FIG. 1 shows the invention mounted in a bracket 29 permiting rotation of the entire assembly in a horizontal plane. Link Arm 3 pivots about Stationary Cylinder A and Link Arm 4 pivots about arm 3 and their common Compensating Cylinder B in a vertical plane.

This range of motion allows the load W (Item of interest) to be moved to any desired position within the range of this mechanism.

A stable vertical position of load W is maintained by the rigidity of arms 3 & 4 and the tensile forces that exist in a portion of Cable 1 that exists between cable clamp stop 14, and Cylinder C. Since the capstan cylinder is locked to its Stationary Axle 10 by Locking Cylinder D, the tensile segment between J4 and C is fixed in its length, thus forming a defined constrained linkage.

To reposition the configuration one has only to depress Release Lever 6 this in turn will rotate locking cylinder D out of frictional contact with capstan C allowing it to rotate as required by cable 1, when the linkage position is changed.

When position change is completed and release lever 6 is released Bias Spring 7 will rotate locking cylinder or cam D into its locking mode, a new stable state is established.

Spring 5 not only provides a minimal tensile force but with Tension Adjuster 23 also establishes circuit continuity of cable 1 to provide a retractile force for cable 1 during repositioning. Tension Adjuster 23 provides an adjustment to alter the force of spring 5. Guide roller 25 promotes adequate cable 1 contact to capstan cylinder C. Locking Pin 17 is fixed to arm 4 and Capstan axle 10 to prevent its rotation.

It should be noted that Release Lever 6 could be located on the underside of arm 4, however the sense of the cable 1 winding over the capstan cylinder would have to be reversed as would Appliance Adapter 16.

DESIGN BASIS FOR INVENTION

Figure 5:
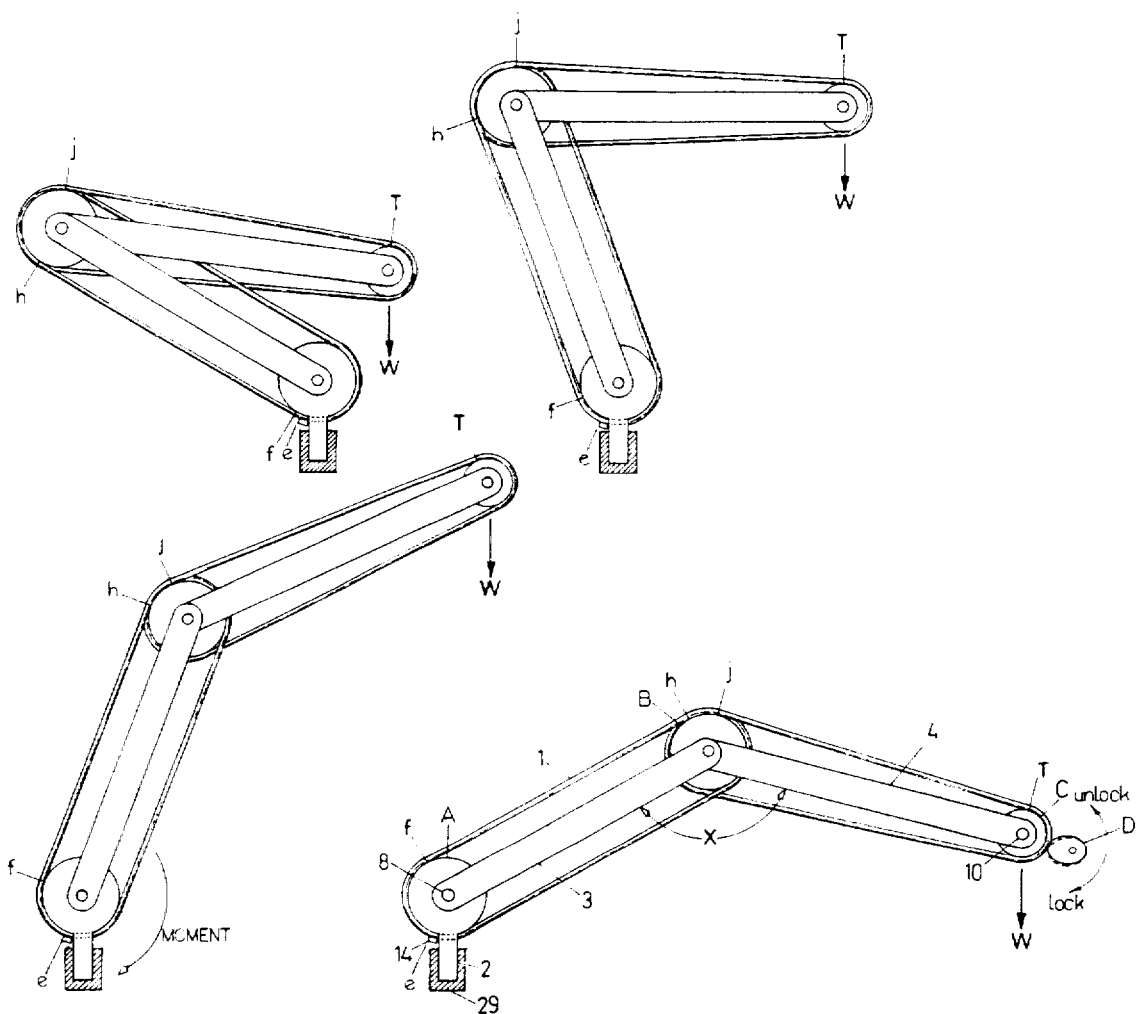
FIG. 5. Is a symbolic plan view to illustrate the basic theory that this invention is based upon.

In order to more readily understand the operation of this invention the following illustration shown in FIG. 5 will define the basic premise for its implemention.

FIG. 5 shows four various configurations that are possible with this mechanism, although it assumes other positions. It is a symbolic pictorial, however the nomenclature is common to the other figures describing this invention. The purpose of these drawings is to show how a segment of cable 1 varies in length with changes in configuration of this mechanism. The segment of cable 1 in question is defined by tangent points e,f,h,j, and T. Since segments f to h and j to T are constant defined by the length of link arms 3 & 4 the variation in length is entirely due to variation of circumferential segments e to f and h to j. The magnitude of variation being affected by the size of the diameters of cylinders A & B and the mechanism configuration.

The larger these diameters are made the more significant changes in length of total segment e,f,h,j,T will occur. It is important to note this length of segment can be fixed by cable clamp 14 and locking cam D. Having this length fixed and applying load W as shown in FIG. 5 will keep this segment in tension which will keep the mechanism in a defined configuration.

As long as the load W maintains a clockwise moment of force about axle 8 this segment will remain in tension and maintain its configuration. To change the configuration locking cam D should be released and the mechanism repositioned and and locked again. It should be noted that the entire circumferential length of cable 1 is a constant and independent of position configuration of the mechanism. The lengths of arms 3 & 4 are proportioned such that a clockwise moment is assured about axle 8. Clockwise as being defined by the illustration in FIG. 5, that is in a sense to keep the cable segment e,f,h,j,T in tension. Indicated Angle X is limited to less than 180 degrees. Link arms 3 & 4 are of rigid material.

Cable 1 has sufficient turns around capstan C to form an effective driving connection between these two elements. Minimal tensile force is provided by Tension Spring 5, which is in the cable circuit with additional tensile force provided by torque moment about 8 as a result of gravitational force of load W. These combined tensile forces provide sufficient friction between cable 1 and cylinder C to effect a bond.

To better understand the locking action of C & D FIG. 10 an isolated view of the pertinent items are shown. With refernce to this pictorial, it should be noted that the tensile force (due to load W) induced in cable 1 tends to impart a clockwise rotation to capstan cylinder C. In frictional contact with C is eccentric locking cylinder D. This condition is insured by by the force of bias spring 7 being applied to release lever 6. Release lever 6 is part of cylinder D. The tensile force of the load due to load W tends to rotate C & D into closer and tighter contact between C & D. This tendency increases these reactive forces of these elements (C & D) greatly increasing the friction betwwen C and its stationary axle 10. The result is that C cannot rotate and remains in a locked position. This action is regenerative in that the greater tendency to rotate C & D into this position the stronger their reactive forces become.

Compensating Cylinder B is free to rotate on its axle 20 so as not to inhibit any motion of cable 1.

The configuration of the flexible element 1 in FIG. 2 maintains the total length of element 1 a constant, independent of position of link arms 3 & 4. This allows spring 5 to maintain a constant minimum tension of 1.

Alternate paths of element 1 are shown in FIGS. 6 and 7.

FIG. 6, will allow the spring 5 to be extended with the rotation of arm 3, thus increasing the minimum retractive tensile force.

FIG. 7, allows the length of spring 5 to be varied with both extensions of arms 3 & 4, thus increasing the minimal retractive force.

DESCRIPTION OF PREFERRED EMBODIMENTS

The invention is shown in FIG. 1 mounted in a fixed stationary bracket 29. Spindle 2 which is part of the invention is allowed to rotate in this bracket in the horizontal plane as indicated. This permits rotation of the entire assembly in the horizontal plane. Rigidly fixed to spindle 2 is stationary cylinder A, also see FIGS. 2 & 3. Main Link Arm 3 is allowed to rotate about cylinder A by virtue of sharing a common pivot which is Arm Axle 8.(FIG. 2) This rotation is in the vertical plane. Opposite cylinder A, at the other end of link arm 3, is mounted Outer Link Arm 4 and Compensating Cylinder B. They share a common pivot by a second arm axle 8. This permits outer link arm 4 to rotate about this axis in a vertical plane. At the extremity opposite cylinder B on the outer link arm 4 is mounted Appliance Adapter 16, this afixes and supports symbolic load W. At this extremity is also located the control Release Lever 6. With special reference to FIGS. 2,3 & 4 other items of the invention can be shown. Item 1 a flexible non-elongational cable is rigidly fixed to cylinder A by two clamps 14, then cable 1 continues in clockwise and upward direction to Compensating Cylinder B, then in the clockwise direction over B to and over the Guide Roller 24 and under a Capstan Cylinder Pulley C, then counter clockwise for several revolutions around capstan pulley C back upwards to and under cylinder B. It then continues in a clockwise sense up around B then downward to attachment to Tension Spring 5. The other end of spring 5 is connected to Tension Adjuster 23 whose other end is connected to cable 1 that is rigidly fixed to cylinder A.

Guide roller 24 revolves about its Guide Roller Axle 25 that is attached to outer link arm 4 by two screws 26. The capstan cylinder revolves around Capstan Stationary Axle 10 that fixes its location to arm 4 by Capstan Axle Locater 22. Locking Pin 17 prevents axle 10 from rotating relative arm 4. Adjacent to capstan cylinder C is Locking Cylinder or Cam D which has limited rotation around Cam Locking Axle 11 that is fixed to arm 4 by two screws 27. Part of cylinder D or afixed to it is Release Lever 6. Release lever 6 is in contact with Bias Spring 7 that is contained within Appliance Adapter 16 which is rigidly fixed to arm 4 by Adapter Screws 28. Other items are Main Arm Motion Limit Pin 21.

All items except the flexible element are constucted of solid rigid materials appropriate to perform stated functions.

The preferred material for cable 1 is a multi-strand metallic cable of sufficient strength so as not to elongate appreciably under its applied tensile forces. Cylinders A & B are of significant diameter so as to affect the circumferential length of segment e,f,h,j,T (FIG. 5) of cable 1 when the position of the device is varied.

Axle 20 is made slightly longer than cylinder B to insure freedom of any side friction forces that may result from its assembly into the invention. Friction Bearing Washers 19 are inserted betwwen cylinder axle 20 and link arm 4 also Friction Bearing Washers 12 are inserted between link arm 3 and link arm 4 also Friction Bearing Washers 18 are inserted betwwen Cylinder A and link arm 3. Washers 12,18, & 19 are of a suitable material to provide smooth predictable friction betwwen their respective parts and also to reduce wear of these parts. Link arm 3 is joined to A and B by its axle 8 and axle retainer 9. Interposed between 3 and 9 is Spring washer 13. Link arms 3 & 4 are joined together with cylinder B its axle 20 and washers 12 & 19 by axle 8 and its retainer 9. Interposed between 3 & 9 at this end is another spring washer 13.

Cylinders A & B have grooves to act as guides for a cable flexible element.

Cylinder C is recessed to protect element 1 from abrasion by locking cylinder D.

FIG. 8, shows another configuration that employs a metal band 31 as the flexible element. This band 31 is also a spring due to its permanent radius of curvature. It is known as a constant force spring which is available from several spring manufacturers.

This spring 31 (tape or band) is rigidly fastened to the capstan cylinder C which is modified for this purpose. This band 31 is also rigidly fastened to cylinder A. It has sufficient length to permit several revolutions to be wrapped about capstan cylinder C.

When the release lever releases the capstan C, and the position of link arms are varied the varation in length of 31 will be compensated by the retractive force of 31 rotating C to vary the accumalation of coils of 31 about C.

Although an illustrative embodiment of the present invention has been described herein, it is to be understood that various changes and modifications thereof can be effected without departing from the scope or spirit of the invention.

Having thus described the preferred embodiments of this invention, LOCKING ACCESSORY SUPPORT APPARATUS are now claimed to be:

1. A locking accessory support apparatus for fixing an object attached to the support apparatus in a chosen one of various stable positions, the support apparatus comprising:

at least two arms which are linked together in a manner allowing for pivotal movement therebetween and with one arm being mounted to a support therefor, the at least two arms comprising a first arm which is pivotable at a support engaging end about a vertical axis about the support therefor and is further pivotable in a vertical plane and a second arm which is pivotably connected to said first arm by an axle and movable in a vertical plane;

a first cylinder attached to said support and not free to rotate relative thereto;

said first arm being pivotably connected to said first cylinder at said support engaging end and having a second cylinder free to rotate about said axle, and the second arm including a third cylinder free to rotate at a free end thereof;

a tensile member wound completely around said second cylinder and extending about the first and third cylinders, the tensile member being continuous and fixed to said first cylinder; and locking means for fixing said support apparatus in any of said stable positions, said locking means being adapted to engage said third cylinder, whereby said engagement acts as a constraint against rotation of the second and third cylinders.

2. The apparatus of claim 1 including means for allowing said tensile member to assume various fixed lengths, said means comprising:

a spring forming a part of said tensile member.

3. The apparatus of claim 1 wherein contact between the tensile member and said second and third cylinders is frictional to effect a driving connection between said cylinder and said tensile member.

4. The apparatus of claim 1 wherein the locking means comprises:

a freely rotating fourth cylinder with a center of rotation offset from its geometric center; and means for selectively engaging said fourth cylinder against said third cylinder.

* * * * *